US006440387B1

(12) United States Patent
Yankner et al.

(10) Patent No.: US 6,440,387 B1
(45) Date of Patent: Aug. 27, 2002

(54) METHODS FOR DETERMINING RISK OF ALZHEIMER'S DISEASE

(75) Inventors: Bruce A. Yankner, West Newton; Philip Nadeau, Boston, both of MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/239,387

(22) Filed: Jan. 28, 1999

Related U.S. Application Data

(62) Division of application No. 09/046,235, filed on Mar. 23, 1998, now Pat. No. 6,080,778.

(51) Int. Cl.$^7$ .................. A61K 49/00; A61K 31/56
(52) U.S. Cl. ................................... 424/9.1; 514/182
(58) Field of Search .............................. 424/2; 514/182

(56) References Cited

FOREIGN PATENT DOCUMENTS

| WO | WO95/06470 A1 | 3/1995 |
| WO | WO97/48701 A1 | 12/1997 |
| WO | WO98/47518 A1 | 10/1998 |
| WO | WO99/15159 A2 | 4/1999 |
| WO | WO99/38498 A1 | 8/1999 |

OTHER PUBLICATIONS

CA 127:135116, Sparks, 1997.*
CA 113:207679, Allen et al., 1990.*
CA 127:106355, Taniguchi et al., Jul. 1997.*
Frears, et al., "The role of cholesterol in the biosynthesis of beta–amyloid," Neuroreport. 10(8):1699–705 (1999).
Jarvik, et al., "Interactions of apolipoprotein E genotype, total cholesterol level, age, and sex in prediction of Alzheimer's disease: a case–control study," Neurology. 45(6):1092–6 (1995).
Wisniewski, et al., "Is Alzheimer's disease an apolipoprotein E amyloidosis?" Lancet. 345(8955):956–8 (1995).
Brown, et al., "A receptor–mediated pathway for cholesterol homeostasis," Science. 232(4746):34–47 (1986).
Busciglio, et al., "Generation of β–amyloid in the secretory pathway in neuronal and nonneuronal cells," Proc. Nat. Acad. Sci. 90, 2092–2096 (1993).
Farrer, et al., "Assessment of Genetic Risk for Alzheimer's Disease among First–Degree relatives," Ann. Neurol. 25: 485–492 (1989).
Goate, et al., (1991) "Segregation of a missense mutation in the amyloid precursor protein gene with familial Alzheimer's disease," Nature 349, 704–706).

Mann and Esiri, "The pattern of acquisition of plaques and tangles in the brains of patients under 50 years of age with Down's Syndrome," J. Neurol. Sci. 89, 169–179 (1984).
McKhahn, et al., "Clinical diagnosis of Alzheimer's disease: Report of the NINCDS–ADRDA work Group* under th4 auspices of Department of Health and Human Services Task Force on Alzheimer's Disease," Neurology 34:939–944 (1984).
Reiman, et al., "Preclinical Evidence of Alzheimer's Disease in Persons Homozygous for the $\epsilon$4 Allele for Apoliprotein E," N.E.J.Med. 334, 752–758 (1996).
Selkoe, D.J., "Alzheimer's Disease: Genotypes, Phenotype, and Treatments," Science 275, 630–631 (1997)).
Sparks, D.L., "Intraneuronal β–Amyloid Immunoreactivity in the CNS," Neurobiology of Aging. 17, 291–299 (1996).
Strittmatter, et al., "Apolipoprotein E: High–avidity binding to β–amyloid and increases frequency of type 4 allele in late–onset familial Alzheimer disease," Proc. Natl. Acad. Sci. U.S.A. 90:1977–1981 (1993).
Van Duijn, et al., "Familial Aggregation of Alzheimer's Disease and Related Disorder's: A Collaborative Re–Analysis of Case–Control Studies," Int. J. Epidemiol. 20 (suppl 2), S13–S20 (1991).
Yankner, "Mechanisms of Neuronal Degeneration in Alzheimer's Disease," Neuron 16, 921–932. (1996).

* cited by examiner

Primary Examiner—Theodore J. Criares
(74) Attorney, Agent, or Firm—Holland & Knight LLP

(57) ABSTRACT

Blood cholesterol levels are correlated with production of amyloid β protein (Aβ), and are predictors of populations at risk of developing AD. Methods for lowering blood cholesterol levels can be used to decrease production of Aβ, thereby decreasing the risk of developing AD. The same methods and compositions can also be used for treating individuals diagnosed with AD. Methods include administration of compounds which increase uptake of cholesterol by the liver, such as the administration of HMG CoA reductase inhibitors, administration of compounds which block endogenous cholesterol production, such as administration of HMG CoA reductase inhibitors, administration of compositions which prevent uptake of dietary cholesterol, and administration of combinations of any of these which are effective to lower blood cholesterol levels. Methods have also been developed to predict populations at risk, based on the role of cholesterol in production of Aβ. For example, individuals with Apo E4 and high cholesterol, defined as a blood cholesterol level of greater than 200 mg/dl, post menopausal women with high cholesterol levels—especially those who are not taking estrogen, or individuals which high blood cholesterol levels who are not obese are all at risk of developing AD if blood cholesterol levels are not decreased.

6 Claims, No Drawings

METHODS FOR DETERMINING RISK OF ALZHEIMER'S DISEASE

This application is a divisional of U.S. Ser. No. 09/046,235 filed Mar. 23, 1998 now U.S. Pat. No. 6,080,778.

BACKGROUND OF THE INVENTION

The United States government has certain rights in this invention by virtue of National Institutes of Health grant number RO1NS33325 to Bruce A. Yankner.

Alzheimer's disease (AD) is the most common cause of dementia in the aged population. The accumulation of large numbers of senile plaques containing the 40–42 amino acid amyloid β protein (Aβ) is a classic pathological feature of AD. Both genetic and cell biological findings suggest that the accumulation of Aβ in the brain is the likely cause of AD (Yankner, B. A. (1996) Neuron 16, 921–932.; Selkoe, D. J. Science 275, 630–631 (1997)). Strong genetic evidence in support of the pathogenic role of Aβ came from the observation that individuals who inherit mutations in the amyloid precursor protein almost invariably develop AD at an early age. These mutations increase the production of a long variant of the Aβ peptide that forms senile plaques in the brain (Goate et al., (1991) Nature 349, 704–706). Mutations and allelic variations in other genes that cause AD, including the presenilins and apolipoprotein E, also result in increased production or deposition of the Aβ peptide. Reiman, et al. (1996) N.E.J.Med. 334, 752–758, reported that in middle age, early to mid 50's, individuals who are homozygous for the Apo E4 gene have reduced glucose metabolism in the same regions of the brain as in patients with Alzheimer's disease. These findings suggest that the pathological changes in the brain associated with this gene start early. Furthermore, individuals with Down's syndrome overexpress the amyloid precursor protein, develop Aβ deposits in the brain at an early age, and develop Alzheimer's disease at an early age. Finally, the Aβ protein has been demonstrated to be highly toxic to nerve cells. Thus, it is widely believed that drugs which decrease the levels of Aβ in the brain would prevent Alzheimer's disease.

The known genetic causes of AD can account for only a small proportion of the total number of cases of AD. Most cases of AD are sporadic and occur in the aged population. A major goal of research is the identification of environmental factors that predispose to AD that would be amenable to therapeutic measures.

It is therefore an object of the present invention to provide methods for predicting populations at risk of developing AD.

It is another object of the present invention to provide diagnostics and pharmaceuticals to decrease the production of amyloid β protein (Aβ), and thereby to prevent or reduce the liklihood of developing AD.

It is a further object of the present invention to provide pharmaceutical treatments to treat AD in patients having the neuropsychiatric or diagnostic criteria for AD.

SUMMARY OF THE INVENTION

Blood cholesterol levels are correlated with production of amyloid β protein (Aβ), and are predictors of populations at risk of developing AD. Methods for lowering blood cholesterol levels cain be used to decrease production of Aβ, thereby decreasing the risk of developing AD. The same methods and compositions can also be used for treating individuals diagnosed with AD. Methods include administration of compounds which increase uptake of cholesterol by the liver, such as the administration of HMG CoA reductase inhibitors, administration of compounds which block endogenous cholesterol production, such as administration of HMG CoA reductase inhibitors, administration of compositions which prevent uptake of dietary cholesterol, and administration of combinations of any of these which are effective to lower blood cholesterol levels. Methods have also been developed to predict populations at risk, based on the role of cholesterol in production of Aβ. For example, individuals with Apo E4 and high cholesterol, defined as a blood cholesterol level of greater than 200 mg/dl, post menopausal women with high cholesterol levels—especially those who are not taking estrogen, or individuals which high blood cholesterol levels who are not obese are all at risk of developing AD if blood cholesterol levels are not decreased. In the preferred embodiment, individuals with these risk factors are treated to lower blood cholesterol levels prior to developing any mental impairment attributable to AD, based on accepted neuropsychiatric and diagnostic criteria in clinical practice. Treatment is based on administration of one or more compositions effective to lower cholesterol blood levels at least 10%, which is believed to be sufficient to decrease production of Aβ.

Diagnostic kits based on the discovery of these risk factors include reagents for measurement of cholesterol, total lipoproteins, and/or Apo E4.

The examples demonstrate the use of HMG CoA reductase inhibitors to treat Alzheimer's disease. Rats fed a high cholesterol diet show increased levels of the Alzheimer's disease Aβ protein in the brain. Cholesterol has been shown to increase the amount of Aβ in human neurons in culture. The HMG CoA reductase inhibitors reduce cholesterol production. Several different HMG CoA reductase inhibitors, including lovastatin, simvastatin, fluvastatin, pravastatin and compactin, significantly inhibit the level of Aβ production in human neuronal cultures.

DETAILED DESCRIPTION OF THE INVENTION

I. Methods for Predicting Populations at Risk for AD

Individuals at increased risk for Aβ accumulation and Alzheimer's disease are those who carry a copy of the apolipoprotein E4 gene (Strittmatter et al., (1993) Proc. Natl. Acad. Sci. U.S.A. 90, 1977–1981), those with trisomy 21 (Down's syndrome) (Mann and Esiri, (1989) J. Neurol. Sci. 89, 169–179)), and individuals who carry a mutation in one of the genes that encode the amyloid precursor protein, presenilin-1 or presenilin-2 (reviewed in Yankner, 1996). In addition, individuals with a family history of Alzheimer's disease have been documented to be at increased risk of Alzheimer's disease (Farrer et al., (1989) Ann. Neurol. 25, 485–492; van Duijn et al., (1991) Int. J. Epidemiol. 20 (suppl 2). S13–S20), and could therefore benefit from prophylactic treatment with an HMG CoA reductase inhibitor.

Methods have also been developed to predict populations at risk, based on the role of cholesterol in production of Aβ. Several risk factors for developing AD have been identified. These include:

(1) individuals with Apo E4 and high cholesterol, defined as a blood cholesterol level of greater than 200 mg/dl, (2) post menopausal women with high cholesterol, especially those who are not taking estrogen, (3) young individuals with high blood cholesterol levels who are not obese (age 48–65 yrs), (4) individuals with high blood cholesterol levels who have a family history of AD, (5) individuals with high blood cholesterol levels who have a family history of AD, and (6) all adult individuals with Down's syndrome.

These individuals are all at risk of developing AD if blood cholesterol levels are not decreased. In the preferred embodiment, individuals with these risk factors are treated to lower blood cholesterol levels prior to developing any mental impairment attributable to AD using accepted neuropsychiatric and diagnostic criteria for probable Alzheimer's disease (McKhahn et al. (1984) Neurology 34:939–944).

Individuals can be screened using standard blood tests for cholesterol, ApoE4, and/or total lipoprotein levels, as well as by taking a medical and family history. In addition, over the counter immunoassay tests can be used by individuals who may be at risk, so that they can seek further medical advise. These immunoassay kits can be qualitative and/or quantitative for elevated cholesterol, total lipoproteins, and Apo E4.

II. Methods of Treatment to Decrease Production of Aβ.

Methods for lowering blood cholesterol levels can be used to decrease production of Aβ, thereby decreasing the risk of developing AD. The same methods can also be used to treat patients who have already been diagnosed with AD. Methods include administration of compounds which increase uptake of cholesterol by the liver, such as the administration of HMG CoA reductase inhibitors, administration of compounds which. block endogenous cholesterol production, such as administration of HMG CoA reductase inhibitors, administration of compositions which prevent uptake of dietary cholesterol, and administration of combinations of any of these which are effective to lower blood cholesterol levels.

The examples indicate that several different HMG CoA reductase inhibitors reduce the production of Aβ. HMG CoA reductase inhibitors may act to lower cholesterol at several different levels. For example, HMG CoA reductase inhibitors have been shown to lower blood cholesterol levels by upregulating lipoprotein clearance receptors in the liver (Brown and Goldstein, (1986) Science 232, 3447). In addition, HMG CoA reductase inhibitors will directly inhibit cholesterol synthesis in neurons. Since every HMG CoA reductase inhibitor tested reduces Aβ production, it is anticipated that new members of this class of drugs will also inhibit Aβ production. Furthermore, since increased dietary cholesterol increases Aβ in the brain, drugs which act through other mechanisms to reduce cholesterol will also inhibit Aβ production.

Representative CoA reductase inhibitors include the statins, including lovastatin, simvastatin, compactin, fluvastatin, atorvastatin, cerivastatin, and pravastin. These are typically administered orally.

Compounds which inhibit cholesterol biosynthetic enzymes, including 2,3-oxidosqualene cyclase. squalene synthase, and 7-dehydrocholesterol reductase, can also be used.

Representative compositions which decrease uptake of dietary cholesterol include the bile acid binding resins (cholestyramine and colestipol) and the fibrates (clofibrate). Probucol, nicotinic acid, garlic and garlic derivatives, and psyllium are also used to lower blood cholesterol levels. Probucol and the fibrates increase the metabolism of cholesterol-containing lipoproteins. The cholesterol-lowering mechanism of nicotinic acid is not understood.

Although the preferential route of administration of HMG CoA reductase inhibitors would be oral, the drugs could also by administered by intravenous, subcutaneous or intramuscular routes. In some cases, direct administration into the cerebrospinal fluid may be efficacious.

III. EXAMPLES

Prior to the studies described in the following examples, the relationship between cholesterol and Aβ levels in the brain was unknown. In one study, rabbits which were fed a high cholesterol diet showed increased immunocytochemical staining of brain neurons with an antibody to Aβ. However, this antibody was not specific for Aβ, and could cross-react with other metabolites of the amyloid precursor protein (Sparks, D. L. (1996) Neurobiology of Aging. 17, 291–299). The studies in the following examples demonstrate that: rats fed a high cholesterol diet show increased levels of the Alzheimer's disease Aβ protein in the brain; cholesterol increases the amount of Aβ in human neurons in culture; HMG CoA reductase inhibitors reduce cholesterol production; and several different HMG CoA reductase inhibitors, including lovastatin, simvastatin, fluvastatin, pravastatin and compactin, significantly inhibit the level of Aβ production in human neuronal cultures.

Example 1: Cholesterol Increases the Level of Aβ in Human Neuronal Cultures.

Busciglio et al., (1993) Proc. Nat. Acad. Sci. 90, 2092–2096, described the production of Aβ by human cortical neurons in culture . To determine whether cholesterol can affect the production of Aβ, primary human brain cultures were established from the cortex of 16–20 week fetal abortuses, and the neurons incubated in the absence or presence of very low density lipoprotein (VLDL), low density lipoprotein (LDL) or high density lipoprotein (HDL) particles isolated from human plasma. These lipoprotein particles are the physiological vehicles for the transport of cholesterol to cells. The effects of the different lipoprotein particles on the levels of Aβ in the human cortical cultures was determined. The human cortical cultures were maintained in serum-free Dulbecco's Modified Eagle's Medium (DMEM) with N2 supplements (a serum-free supplement that supports neuronal viability). The medium was then changed to the same medium (controls) or medium supplemented with VLDL, LDL, or HDL particles. After incubation for 48–72 hours, Aβ was measured by immunoprecipitation of the culture medium with a polyclonal antibody to Aβ (B12), followed by Western blotting with a mohoclonal antibody to Aβ (6E10). The Western blots were developed either by the enhanced chemiluminescence method or by addition of an $^{25}$I-labeled secondary antibody and phosphorimager scanning. The bands corresponding to the 40 and 42 amino acid form of Aβ were analyzed quantitatively using a computer software program. Control human cortical cultures produced basal levels of Aβ. Exposure of the human cortical cultures to VLDL, LDL or HDL particles increased the levels of both the 40 and 42 amino forms of Aβ. These results suggest that the major classes of cholesterol-containing lipoproteins all act to increase production of Aβ in human neurons.

It was then determined whether lipoprotein particles containing apolipoproteins E or A1 were able to increase Aβ production. To address this question, synthetic lipoprotein particles containing these proteins were created. Particles containing either apolipoprotein E or A1 increased the level of Aβ in the human cortical cultures.

These results indicate that a variety of different cholesterol carrying lipoprotein particles can increase the production of Aβ in primary human neuronal cultures.

Example 2: Dietary Cholesterol Increases Aβ Levels in the Brain

After establishing that cholesterol-carrying lipoprotein particles increase Aβ in cultures of human neurons, it was determined whether dietary cholesterol increases the level of Aβ in the brain in vivo. Increased dietary intake of cholesterol is known to increase circulating levels of lipoprotein particles, which in turn increases the delivery of cholesterol to cells. These experiments were performed on 20 month old rats. The rats were fed a low cholesterol diet (0.1% cholesterol) or a high cholesterol diet (5% cholesterol). After 10 weeks, the animals were sacrificed and the cortex was removed for measurement of Aβ levels. Aβ was assayed by immunoprecipitating cortical homogenates with the Aβ antibody B12, followed by Western blotting with the commercially available Aβ monoclonal antibody 4G8.

Resolution of the Aβ isolated from rat cerebral cortex by electrophoretic separation on gels showed that Aβ levels were significantly increased by about 50% in the group of rats fed the high cholesterol diet relative to the group of rats fed the low cholesterol diet. These findings indicate that dietary cholesterol increases the amount of Aβ in the brain. It is noteworthy that the approximately 50% increase in Aβ in the brain induced by a high cholesterol diet is similar to the increase in Aβ which occurs in Down's syndrome, which is known to predispose to the development of Alzheimer's disease.

Example 3: HMG CoA Reductase Inhibitor, Inhibit the Production of Aβ by Human Neurons The HMG CoA reductase inhibitors have been used in humans to decrease plasma levels of cholesterol in patients at risk for heart disease. The discovery that cholesterol increases the amount of Aβ in the brain led to this investigation to determine whether the HMG CoA reductase inhibitors may be therapeutically efficacious for Alzheimer's disease by inhibiting the production of Aβ. Human cortical neuronal cultures were established from 18 weeks gestation normal fetal cortical tissue as described above and maintained in a culture medium comprised of DMEM containing N2 supplements. After one week, the culture medium was changed to DMEM+N2 supplements (control), or DMEM+N2 supplements+either 100 μM lovastatin, 100 μM simvastatin, 100 μM compactin, 100 μM fluvastatin, or 1 mM pravastatin. after incubation for 48 hours, the cultured cells were harvested and the levels of Aβ were assayed, as described above.

Aβ was isolated from the culture medium from human cortical neuronal cultures and resolved by electrophoresis in gels. These results demonstrate that human neurons treated with either lovastatin, simvastatin, compactin, fluvastatin or pravastatin have significantly decreased levels of Aβ relative to controls. These results indicate that HMG CoA reductase inhibitors decrease the production of Aβ by human neurons.

The finding that HMG CoA reductase inhibitors inhibit Aβ production by human cortical cells supports the use of this class of drugs for reducing the levels of Aβ in individuals with Alzheimer's disease or at risk of developing Alzheimer's disease.

Modifications and variations of the methods and compositions for prediction of the liklihood of developing AD, and for preventing and/or treating AD, will be obvious to those skilled in the art. These modifications and variations are intended to come within the scope of the appended claims.

We claim:

1. A method for predicting if a person is at risk of developing Alzheimer's Disease but has not yet developing the clinical signs of Alzheimer's Disease comprising determining if the person has elevated blood levels of cholesterol, wherein the level is 200 mg/dl or greater.

2. The method of claim 1 further comprising determining if the person carries the apolipoprotein E4 gene.

3. The method of claim 1 further comprising determining if the person has trisomy 21 (Down's syndrome).

4. The method of claim 1 further comprising determining if the person carries one or more mutations in the genes that encode amyloid β protein, amyloid precursor protein, presenilin-1 or presenilin-2.

5. The method of claim 1 further comprising determining if the person has a family history of Alzheimer's disease or dementing illness.

6. The method of claim 1 further comprising determining if the person is a post menopausal woman with high cholesterol.

* * * * *